US012558296B2

(12) United States Patent
Nakamura et al.

(10) Patent No.: US 12,558,296 B2
(45) Date of Patent: *Feb. 24, 2026

(54) OIL-IN-WATER EMULSION GEL COMPOSITION

(71) Applicant: L V M H RECHERCHE, Saint-Jean de Brave (FR)

(72) Inventors: Kyosuke Nakamura, Tokyo (JP); Miyako Kitamura, Tokyo (JP); Koichi Hata, Tokyo (JP)

(73) Assignee: L V M H RECHERCHE, Saint-Jean de Brave (FR)

( * ) Notice: Subject to any disclaimer, the term of this patent is extended or adjusted under 35 U.S.C. 154(b) by 619 days.

This patent is subject to a terminal disclaimer.

(21) Appl. No.: 17/621,103

(22) PCT Filed: Jun. 25, 2019

(86) PCT No.: PCT/IB2019/000761
§ 371 (c)(1),
(2) Date: Dec. 20, 2021

(87) PCT Pub. No.: WO2021/048577
PCT Pub. Date: Mar. 18, 2021

(65) Prior Publication Data
US 2022/0347063 A1     Nov. 3, 2022

(51) Int. Cl.
| | |
|---|---|
| *A61K 8/06* | (2006.01) |
| *A61K 8/04* | (2006.01) |
| *A61K 8/29* | (2006.01) |
| *A61K 8/34* | (2006.01) |
| *A61K 8/41* | (2006.01) |
| *A61K 8/87* | (2006.01) |
| *A61Q 19/00* | (2006.01) |

(52) U.S. Cl.
CPC .............. *A61K 8/062* (2013.01); *A61K 8/042* (2013.01); *A61K 8/29* (2013.01); *A61K 8/345* (2013.01); *A61K 8/41* (2013.01); *A61K 8/87* (2013.01); *A61Q 19/001* (2013.01)

(58) Field of Classification Search
None
See application file for complete search history.

(56) References Cited

U.S. PATENT DOCUMENTS

| | | | |
|---|---|---|---|
| 11,298,301 B2 * | 4/2022 | Kitamura | A61K 8/42 |
| 2002/0155076 A1 | 10/2002 | Lanzendorfer et al. | |
| 2012/0251603 A1 * | 10/2012 | Yamada | A61K 8/8158 424/59 |
| 2017/0326060 A1 * | 11/2017 | Matsuo | A61Q 1/04 |
| 2020/0306151 A1 | 10/2020 | Takahashi et al. | |

FOREIGN PATENT DOCUMENTS

| | | |
|---|---|---|
| EP | 3173064 A1 | 5/2017 |
| EP | 3213743 A1 | 9/2017 |
| FR | 2985180 A1 | 7/2013 |
| FR | 3059545 A1 | 6/2018 |
| JP | 2002-087931 A | 3/2002 |
| JP | 2006-290762 A | 10/2006 |
| JP | 2014-105207 A | 6/2014 |
| JP | 2015-174849 A | 10/2015 |
| JP | 2017-081868 A | 5/2017 |
| JP | 2017-105766 A | 6/2017 |
| JP | 2018-076308 A | 5/2018 |
| JP | 2019-64966 A | 4/2019 |
| WO | WO-2014/185317 A1 | 11/2014 |
| WO | WO-2014/195265 A1 | 12/2014 |
| WO | WO 2019/066057 A1 | 4/2019 |
| WO | WO 2020/128557 A1 | 6/2020 |

OTHER PUBLICATIONS

International Application No. PCT/IB2019/000761, International Search Report and Written Opinion, mailed Apr. 1, 2020.
Japanese Office Action for Japanese Application No. 2024-096478, dated Aug. 5, 2025, with English translation.
European Communication pursuant to Article 94(3) EPC for European Application No. 19 780 339.8, dated Nov. 3, 2025.

* cited by examiner

*Primary Examiner* — Ali Soroush
*Assistant Examiner* — Afua Bamfoaa Boateng
(74) *Attorney, Agent, or Firm* — Birch, Stewart, Kolasch & Birch, LLP

(57) ABSTRACT

The present invention relates to an oil-in-water emulsion gel cosmetic composition comprising an oil agent, water, a polyol, an anionic surfactant, an amphiphilic polymer and a coloring material.

11 Claims, No Drawings

OIL-IN-WATER EMULSION GEL COMPOSITION

CROSS REFERENCE TO RELATED APPLICATIONS

This Application is a U.S. National Stage of International Patent Application No. PCT/IB2019/000761 filed Jun. 25, 2019, the disclosures of which is incorporated herein by reference in their entirety.

TECHNICAL FIELD

The present invention relates to an oil-in-water emulsion gel composition.

BACKGROUND ART

Oil-in-water emulsions containing appropriate amounts of oil agents in formulations provide a protective film effect, and are therefore desirable for use in cosmetics and the like.

Japanese Patent Application Publication No. 2002-087931, for example, discloses an oil-in-water emulsion composition comprising water, a hydrophilic surfactant, a liquid oil component and solid fat, wherein the light transmittance at 550 nm is 50% or higher and the viscosity at 25° C. is 200 to 1,000,000 mPa·s. Such oil-in-water emulsion exhibits a high transparency in appearance and may be used for example as hair cosmetics, shaving cosmetics and body lotions. In addition, Japanese Patent Application Publication No. 2017-105766 (or its equivalent EP3173064 A1) discloses an oil-in-water emulsion gel composition having excellent transparency and excellent stability over time comprising (A) one or more liquid oils selected from among hydrocarbon oils, aliphatic esters and silicone oils in an amount of 15% or higher with respect to total amount of oil-in-water-emulsion gel composition, (B) one or more nonionic emulsifiers having an HLB value less than or equal to 7 (HLB≤7), selected from among (poly)glyceryl fatty acid (esters) and POE hydrogenated castor oil, (C) sucrose fatty acid esters, (D) ionic surfactants with glutamic acid as a hydrophilic group, and (E) water, wherein a total content ratio of (B), (C) and (D) with respect to (A) is from 0.1 to 0.5 by mass. But none of these documents disclose an oil-in-water emulsion gel composition exhibiting both a care effect and a makeup effect with color vividness.

TECHNICAL PROBLEM

For an oil-in-water cosmetic containing a coloring material such as a dye, the applied film formed by coating the cosmetic (makeup film) is preferably one with excellent color vividness. From the viewpoint of easily exhibiting a care effect and makeup effect as well, the oil-in-water cosmetic preferably has excellent stability and a nourishing effect.

But when the oil agent content of an oil-in-water cosmetic is increased in order to impart a high nourishing effect, it is often necessary to include a large amount of thickener, from the viewpoint of maintaining high stability. When an excessive amount of thickener is used, however, a non-homogeneous or rough applied film tends to form, often impairing the color vividness of the applied film. For this reason it has been difficult to obtain cosmetics that are excellent in terms of all properties including a high nourishing effect, stability of the oil-in-water cosmetic and color vividness of the applied film.

So it is an object of the present invention to provide an oil-in-water gel composition that is excellent in terms of stability, nourishing effect and color vividness of the applied film.

SUMMARY OF THE INVENTION

The present invention provides an oil-in-water emulsion gel composition comprising an oil agent, water, a polyol, an anionic surfactant, an amphiphilic polymer and a coloring material.

Since the oil-in-water emulsion gel composition of the invention includes an oil agent, water, a polyol, an anionic surfactant, an amphiphilic polymer and a coloring material in combination, and it is in gel form, it is excellent in terms of all of the properties including a high nourishing effect, stability of the oil-in-water emulsion gel composition and color vividness of the applied film. This effect is produced by the formulated combination of the invention, but it is the amphiphilic polymer in particular that increases the viscosity of the formulation by interaction between the emulsion particles and anionic surfactant, via its own hydrophobic groups, and effectively contributes to formation of the gel. With the oil-in-water emulsion gel composition of the invention, therefore, it is a goal to achieve drastic improvement in maintaining viscosity over time, when the viscosity is compared immediately after preparation and after standing for one month at 50° C., for example. The oil-in-water emulsion gel composition of the invention therefore exhibits both a care effect and a makeup effect. The oil-in-water emulsion gel composition of the invention can also form a applied film that provides a fresh, light feel.

The present invention also relates to a cosmetic process for caring for and/or making-up keratinic materials, comprising the application onto keratinic materials, in particular onto skin or lips, of the oil-in-water emulsion gel composition according to the invention.

In particular, the cosmetic process provides water fresh sensation, color vividness of applied film and nourishing effect onto keratinic materials, in particular onto skin or lips, on which the composition of the invention is applied.

ADVANTAGEOUS EFFECTS OF INVENTION

According to the invention it is possible to provide a cosmetic composition that is excellent in terms of stability, nourishing effect and color vividness of the applied film.

The cosmetic composition of the invention easily forms a homogeneous applied film, it can therefore easily form a coated film with vivid color even when applied thinly. Moreover, the cosmetic composition of the invention also forms an applied film that imparts a fresh light feeling without sense of dryness.

DETAILED DESCRIPTION OF THE INVENTION

In a particular embodiment, the anionic surfactant is an amino acid-based anionic surfactant, preferably selected from the group consisting of N-stearoylglutamic acid salts, dilauroylglutamic acid lysine salts, and mixtures thereof.

In a particular embodiment, the polyol is a $C_1$-$C_6$ polyol, preferably selected from the group consisting of pentylene glycol, butylene glycol, glycerin, propanediol (1,3-propanediol, propylene glycol or a mixture thereof), dipropylene glycol, sorbitol, and mixtures thereof.

In a particular embodiment, the oil agent(s) total content ranges from 20 mass % to 50 mass % based on the total mass of the oil-in-water emulsion gel composition. By limiting the oil agent content to within this range, the fresh light feel, the color vividness and nourishing effect of the applied film will be even more excellent. In a preferred embodiment, the oil agent(s) total content ranges from 35 mass % to 45 mass % based on the total mass of the oil-in-water emulsion gel composition.

In a particular embodiment, the amphiphilic polymer is selected from the group consisting of a hydrophobic group-modified hydrophilic urethane polymer, (meth)acrylic polymers having a side chain that includes a hydrophilic group and a hydrophobic group, a hydrophobic group-modified hydrophilic polysaccharide, and mixtures thereof. In a particular embodiment, the composition of the invention comprises a hydrophobic group-modified hydrophilic urethane polymer and a (meth)acrylic polymer having a side chain that includes a hydrophilic group and a hydrophobic group. In a particular embodiment, the hydrophobic group-modified hydrophilic urethane polymer comprises a hydrophobic group-modified polyether urethane including polyethylene glycol as a glycol component.

In a particular embodiment, the oil-in-water emulsion gel composition may further comprise a higher aliphatic monohydric alcohol. This will result in even more excellent color vividness of the applied film.

The viscosity of the oil-in-water emulsion gel composition ranges from 20,000 to 400,000 cps at 25° C., in particular from 30,000 to 350,000 cps, preferably from 40,000 to 300,000 cps and more preferably from 50,000 to 250,000 cps at 25° C. If the viscosity of the oil-in-water emulsion gel composition at 25° C. is within these ranges, the color vividness, nourishing effect and stability of the applied film will be even more excellent.

The oil-in-water emulsion gel composition is suitable for use on keratinic materials, in particular for skin or lips and particularly suitable for use on lips.

In a particular embodiment, the oil-in-water emulsion gel composition is obtainable by emulsification at a pressure of 50 MPa or greater.

DESCRIPTION OF EMBODIMENTS

Embodiments for carrying out the invention will now be explained in further detail. However, the present invention is not limited to the embodiments described below. Throughout the present specification, the term "(meth)acrylic" refers to acrylic or methacrylic, and the same applies to analogous backbones.

The oil-in-water emulsion gel composition according to one embodiment comprises an oil agent, water, a polyol, an anionic surfactant, an amphiphilic polymer and a coloring material. A "oil-in-water emulsion gel composition" also named "oil-in-water gel cosmetic" or "oil-in-water emulsion gel cosmetic" or "oil-in water gel-type composition" is an oil-in-water emulsion composition that does not flow for a period of 1 hour under 25° C. conditions when 0.5 g of the oil-in-water emulsion composition has been spread on an inclined surface that is inclined at 30 degrees with respect to the horizontal.

Since the oil-in-water emulsion gel composition is excellent in terms of all of the properties of stability, nourishing effect and color vividness of the applied film, it can be used on the lips or on the skin, in particular on cheeks and over the entire face. It is particularly suitable for use on the lips.

The oil-in-water emulsion gel composition can also be suitably used as a skin care cosmetic and/or a makeup cosmetic. Examples of specific uses of the oil-in-water emulsion gel composition for lips include uses as a liquid lip cream, a liquid lipstick foundation or a liquid lipstick overcoat. An example of a specific use of the oil-in-water emulsion gel composition for cheeks is use as a liquid rouge cosmetic (liquid cheek cosmetic). Examples of specific uses of the oil-in-water emulsion gel composition for the entire face include uses as a foundation, makeup base, concealer or sunscreen.

Oil Agent

The oil agent used is preferably a oil agent which is liquid at ambient temperature (25° C.), and liquid oil agents to be added include polar or non-polar hydrocarbon oil agents and polar or non-polar silicone oil agents. The oil agent may be either a non-volatile oil agent or a volatile oil agent.

Examples of oil agents include isononyl isononanoate, isotridecyl isononanoate, ethylhexyl palmitate, cetyl ethylhexanoate, neopentyl glycol diethylhexanoate, neopentyl glycol dicaprate, triethylhexanoin, glyceryl tri(caprylate/caprate), triisostearin, trimethylolpropane triisostearate, pentaerythrityl tetraethylhexanoate, pentaerythrityl tetraisostearate, polyglyceryl-2 tetraisostearate, propanediol di(caprylate/caprate), propanediol diisostearate, polyglyceryl-6 octacaprylate, and mixtures thereof.

Examples of oil agents also include octyldodecyl lactate, diisostearyl malate, polyglyceryl-2 isostearate, polyglyceryl-2 diisostearate, polyglyceryl-2 triisostearate, ditrimethylolpropane (isostearate/sebacate) oligoester, erythrityl triethylhexanoate, dipentaerythrityl tripolyhydroxystearate, trehalose isostearate esters, dipentaerythrityl pentaisostearate, ethylhexyl hydroxystearate, polyhydroxystearic acid, liquid paraffin, squalane, α-olefin oligomer, vaseline, polyisobutylene, polybutene, isododecane, isohexadecane, heavy liquid isoparaffin, and mixtures thereof.

Silicone oils may also be used as oil agents. Examples of silicone oil agents include dimethylpolysiloxane (dimethicone), methyltrimethicone, methylphenylpolysiloxane, decamethylcyclopentasiloxane, octamethylcyclotetrasiloxane, trimethylsiloxysilicic acid, high-polymerization-degree methylphenylpolysiloxane, and mixtures thereof.

A preferred polar oil agent among these oil agents is polyglyceryl-2 triisostearate, preferred non-polar oil agents are squalane, isododecane, α-olefin oligomer, or mixtures thereof and preferred silicone oil agents are dimethylpolysiloxane (dimethicone), methyltrimethicone, decamethylcyclopentasiloxane, or mixtures thereof.

Other oil agents that may be used in addition to these include oil agent pastes such as cholesteryl hydroxystearate, phytostearyl hydroxystearate, phytostearyl oleate, dipentaerythrityl hexa(hydroxystearate/stearate/rosinate), dipentaerythrityl tetra(hydroxystearate/isostearate), dipentaerythrityl hexahydroxystearate, glyceryl (ethylhexanoate/stearate/adipate), glyceryl tri(caprylate/caprate/myristate/stearate), hydrogenated palm oil, vaseline, dipentaerythrityl hexa(behenate/benzoate/ethylhexanoate), plant oil pastes (vegetable oils), shea butter (*Butyrospermum parkii*), mango seed butter (*Mangifera indica*) avocado butter (*Persea gratissima*), and mixtures thereof.

The oil-in-water emulsion gel cosmetic composition may include one type of these oil agents, or it may include two or more different oil agents. For example, the oil-in-water emulsion gel cosmetic composition may comprise 2 to 6 types of oil agents, or 3 to 4 types of oil agents.

In a particular embodiment, from the viewpoint of even more excellent color vividness of the applied film, and an even more excellent nourishing effect, the oil agent(s) total content with respect to the total mass of the oil-in-water emulsion gel composition may be 20 mass % or greater, 25 mass % or greater, 30 mass % or greater, 35 mass % or greater or 40 mass % or greater, and from the viewpoint of an even more excellent fresh light feel and even more excellent color vividness of the applied film, it may be no greater than 50 mass % or no greater than 45 mass %. In a particular embodiment, from the viewpoint of even greater excellence in terms of the color vividness of the applied film, the nourishing effect and the fresh light feel, the oil agent(s) total content with respect to the total mass of the oil-in-water emulsion gel composition is from 20 mass % to 50 mass %, 25 mass % to 50 mass %, 30 mass % to 50 mass %, 35 mass % to 50 mass %, 40 mass % to 50 mass %, 20 mass % to 45 mass %, 25 mass % to 45 mass %, 30 mass % to 45 mass %, 35 mass % to 45 mass % or 40 mass % to 45 mass %. In a particular and preferred embodiment, the oil agent(s) total content with respect to the total mass of the oil-in-water emulsion gel composition is from 35 mass % to 45 mass %.

In a particular embodiment, from the viewpoint of even more excellent color vividness of the applied film and/or a more excellent nourishing effect, the oil agent(s) may include one or more selected from the group consisting of polar oil agents, non-polar oil agents and silicone oil agents, or it may include 2 or 3 selected from the group consisting of polar oil agents, non-polar oil agents and silicone oil agents, or it may include a polar oil agent, a non-polar oil agent and a silicone oil agent.

The content ratio of a polar oil agent with respect to the total mass of the oil agent(s) may be 1 mass % or greater, 5 mass % or greater, 10 mass % or greater, 20 mass % or greater or 30 mass % or greater and no greater than 100 mass %, no greater than 98 mass %, no greater than 95 mass %, no greater than 80 mass %, no greater than 70 mass %, no greater than 60 mass %, no greater than 50 mass %, no greater than 40 mass % or no greater than 30 mass %, and it may be in the range of 1 to 80 mass %, 5 to 60 mass %, 10 to 50 mass % or 20 to 40 mass %.

The content ratio of a non-polar oil agent with respect to the total mass of the oil agent(s) may be 1 mass % or greater, 5 mass % or greater, 10 mass % or greater, 20 mass % or greater or 30 mass % or greater and no greater than 100 mass %, no greater than 98 mass %, no greater than 95 mass %, no greater than 80 mass %, no greater than 70 mass %, no greater than 60 mass %, no greater than 50 mass %, no greater than 40 mass % or no greater than 30 mass %, and it may be in the range of 1 to 80 mass %, 5 to 60 mass %, 10 to 50 mass % or 20 to 40 mass %.

The content ratio of a silicone oil agent with respect the total mass of the oil agent may be 1 mass % or greater, 5 mass % or greater, 10 mass % or greater, 20 mass % or greater or 30 mass % or greater and no greater than 100 mass %, no greater than 98 mass %, no greater than 95 mass %, no greater than 80 mass %, no greater than 70 mass %, no greater than 60 mass %, no greater than 50 mass %, no greater than 40 mass % or no greater than 30 mass %, and it may be in the range of 1 to 80 mass %, 5 to 60 mass %, 10 to 50 mass % or 20 to 40 mass %.

Water

The oil-in-water emulsion gel cosmetic composition contains water. In a particular embodiment, the water content may be 35 mass % or greater, or 40 mass % or greater, and no greater than 60 mass % or no greater than 50 mass %, based on the total mass of the oil-in-water emulsion gel composition. In a particular embodiment, the water content ranges from 35 mass % to 60 mass %, preferably from 40 mass % to 50 mass %, based on the total mass of the oil-in-water emulsion gel composition.

Polyol

A polyol is an aliphatic compound having two or more hydroxyl groups (—OH). The number of hydroxyl groups in the polyol may be 2 or more, such as 3 or more, and it may be up to 10, up to 8, up to 6 or up to 4 hydroxyl groups. The number of hydroxyl groups in the polyol may be, for example, 2 to 10, 2 to 6 or 2 to 4.

The number of carbon atoms of the polyol may be, for example, one or more, 2 or more or 3 or more, and up to 10, up to 8 or up to 6. The number of carbon atoms of the polyol may be, for example, 2 to 10, 2 to 8 or 2 to 6. The polyol is preferably a $C_1$-$C_6$ polyol, which is a polyol of 1 to 6 carbon atoms.

Examples of polyols include butylene glycol (such as 1,3-butylene glycol), pentylene glycol (such as 1,2-pentanediol), glycerin, propanediol (such as 1,3-propanediol, propylene glycol or their mixtures), dipropylene glycol, sorbitol, and mixtures thereof.

The oil-in-water emulsion gel composition may contain a single type of polyol, or it may contain a combination of two or more different polyols. In a particular embodiment, the composition comprises polyol(s) selected from the group consisting of butylene glycol, pentylene glycol, glycerin, propanediol (1,3-propanediol, propylene glycol or a mixture thereof), dipropylene glycol sorbitol, and mixtures thereof. In particular, it comprises one or more, preferably two or more selected from the group consisting of butylene glycol, pentylene glycol, glycerin, propanediol (1,3-propanediol, propylene glycol or a mixture thereof), dipropylene glycol and sorbitol, and even more preferably it comprises butylene glycol, pentylene glycol, glycerin, propanediol (1,3-propanediol, propylene glycol or a mixture thereof), dipropylene glycol and sorbitol.

In a particular embodiment, the polyol(s) total content may be 1 mass % or greater, 5 mass % or greater, 8 mass % or greater or 10 mass % or greater, and no greater than 25 mass %, no greater than 20 mass % or no greater than 15 mass %, based on the total mass of the oil-in-water emulsion gel cosmetic composition. In a particular embodiment, the polyol(s) total content ranges from 1 mass % to 25 mass %, 5 mass % to 25 mass %, 8 mass % to 20 mass %, 10 mass % to 20 mass % or 10 mass % to 15%, based on the total mass of the oil-in-water emulsion gel composition.

Anionic Surfactant

An anionic surfactant is a surfactant having as its hydrophilic group an ionic dissociable group (anionic dissociable group) that dissociates in water to form an anion. Anionic dissociable groups include carboxyl group (—COOH), sulfo group (—$SO_3H$) and phosphate group (—$OPO(OH)_2$). An anionic surfactant may have a carboxyl group as an anionic dissociable group, from the viewpoint of even greater excellence of the effect of the invention. The number of anionic dissociable groups in the anionic surfactant may be one or more or 2 or more, and up to 5 or up to 4, for example. The number of anionic dissociable groups in the anionic surfactant may be 1 to 5, 2 to 5, 1 to 4 or 2 to 4, for example. The anionic surfactant may also have an aliphatic hydrocarbon group as a hydrophobic group (a group with hydrophobicity). The aliphatic hydrocarbon group may be straight-chain or branched. The aliphatic hydrocarbon group is preferably straight-chain. The number of carbon atoms in the aliphatic hydrocarbon group may be 5 to 30 or 10 to 25.

In a particular embodiment, the anionic surfactant is an amino acid-based anionic surfactant, from the viewpoint of even greater excellence of the effect of the invention. An amino acid-based anionic surfactant is an anionic surfactant having an amino acid residue as a partial structure. Examples of amino acids include glutamic acid and lysine. The anionic surfactant may also have a glutamic acid residue and/or lysine residue. The anionic dissociable group in the anionic surfactant may be the carboxyl group from the amino acid residue.

Examples of amino acid-based anionic surfactants include N-acylglutamic acid salts such as N-lauroylglutamic acid salts, N-myristoylglutamic acid salt (N-myristoyl-L-glutamic acid salts and the like), N-stearoylglutamic acid salts (for example, sodium N-stearoylglutamate); N-acylglycine salts such as N-lauroylglycine salts, N-myristoylglycine salts and N-stearoylglycine salts; N-acylalanine salts such as N-lauroylalanine salts, N-myristoylalanine salts and N-stearoylalanine salts; N-acylaspartic acid salts such as N-lauroylaspartic acid salts, N-myristoylaspartic acid salts and N-stearoylaspartic acid salts; diacylglutamic acid lysine salts such as dilauroylglutamic acid lysine salts (for example, sodium lysine dilauroylglutamate), surfactin sodium, and mixtures thereof.

Other examples of anionic surfactants to be used include fatty acid soaps such as lauric acid salts and palmitic acid salts; phosphoric acid ester salts such as cetylphosphoric acid salts; and long-chain acyl lower alkyl-type taurine salts such as N-cocoyl-N-methyltaurine salts, N-lauroyl-N-methyltaurine salts, N-myristoyl-N-methyltaurine salts, N-stearoyl-N-methyltaurine salts N-cocoyltaurine salts, and mixtures thereof.

In a particular and preferred embodiment, the composition of the invention comprises an amino acid-based anionic surfactant, preferably selected from the group consisting of N-stearoylglutamic acid salts, dilauroylglutamic acid lysine salts and mixtures thereof, and from the viewpoint of even more excellent color vividness of the applied film, it more preferably comprises an N-acylglutamic acid salt N-acylglutamic acid salt such as sodium N-stearoylglutamate.

The anionic surfactant(s) total content may be 0.1 mass % or greater, 0.5 mass % or greater, 0.8 mass % or greater, 1.0 mass % or greater or 1.2 mass % or greater, and no greater than 10 mass %, no greater than 5 mass %, no greater than 4 mass %, no greater than 3 mass %, no greater than 2 mass % or no greater than 1.8 mass %, based on the total mass of the oil-in-water emulsion gel composition. In a particular embodiment, the anionic surfactant(s) total content ranges from 0.1 mass % to 10 mass %, 0.5 mass % to 5 mass %, 0.8 mass % to 4 mass %, 1.0 mass % to 2.0 mass % or 1.2 mass % to 1.8 mass %, based on the total mass of the oil-in-water emulsion gel composition.

Amphiphilic Polymer

The oil-in-water emulsion gel composition comprises an amphiphilic polymer. An amphiphilic polymer is a polymer having both a hydrophobic group and a hydrophilic group.

The hydrophobic groups may be $C_1$-$C_{30}$ hydrocarbon groups, which are typically $C_1$-$C_{30}$ straight-chain or branched alkyl groups. The number of carbon atoms is preferably 6 to 30 and more preferably 12 to 24.

The straight-chain or branched alkyl groups may be dodecyl (lauryl), tridecyl, tetradecyl, pentadecyl, hexadecyl, heptadecyl, octadecyl, nonadecyl, eicosyl, docosyl (behenyl) or decyltetradecyl groups.

The hydrophilic group may be an ionic dissociable group (for example, a carboxyl or sulfo group), or it may be a nonionic dissociable group. The amphiphilic polymer may have a polyalkylene glycol (for example, polyethylene glycol or polypropylene glycol), polyglycerin, or a residue of a hydrophilic molecule such as a polysaccharide, as the hydrophilic group.

In a particular embodiment, the amphiphilic polymer is selected from the group consisting of a hydrophobic group-modified hydrophilic urethane polymer, a (meth)acrylic polymer having a side chain that includes a hydrophilic group and a hydrophobic group, a hydrophobic group-modified hydrophilic polysaccharide, and mixtures thereof. In particular, the composition of the invention comprises one or more amphiphilic polymer(s) selected from the group consisting of hydrophobic group-modified hydrophilic urethane polymers, (meth)acrylic polymers having a side chain that includes a hydrophilic group and a hydrophobic group, and hydrophobic group-modified hydrophilic polysaccharides, and preferably it comprises one or more selected from the group consisting of hydrophobic group-modified hydrophilic urethane polymers and (meth)acrylic polymers having a side chain that includes a hydrophilic group and a hydrophobic group. In a particular and preferred embodiment, the composition of the invention comprises a hydrophobic group-modified hydrophilic urethane polymer and a (meth) acrylic polymer having a side chain that includes a hydrophilic group and a hydrophobic group. The term "hydrophobic group-modified" for an amphiphilic polymer means that a hydrophobic group is attached to the molecule.

Hydrophobic group-modified hydrophilic urethane polymers include hydrophobic group-modified polyether urethanes containing polyethylene glycol as a glycol component. Useful urethane polymers of this type include ones having the aforementioned hydrophobic groups introduced at the ends or side chains of a hydrophilic urethane polymer having PEO blocks, PEO/PPO blocks, PEO/PPO/PEO blocks or PPO/PEO/PPO blocks. PEO stands for polyoxyethylene and PPO for polyoxypropylene, and these may be referred to as PEG and PPG, respectively. The isocyanate forming a urethane may be an aromatic isocyanate, aliphatic isocyanate or alicyclic isocyanate.

examples of hydrophobic group-modified hydrophilic urethane polymers include (PEG-240/decyl tetradeceth-20/ HDI) copolymer (trade name: ADEKA NOL GT-700), (PEG-150/decyl alcohol/saturated bismethylenediphenyl isocyanate (SMDI)) copolymer (trade name: Aculyn 44) and (PEG-150/stearyl alcohol/SMDI) copolymer (trade name: Aculyn 46N).

The term "(meth)acrylic polymer" for an amphiphilic polymer means that it has a (meth)acrylic monomer as the main monomer unit.

Examples of (meth)acrylic polymers having a side chain that includes a hydrophilic group and a hydrophobic group include (meth)acrylic polymers having a side chain including a hydrophilic group and including no hydrophobic groups (hydrophilic side chain) and a side chain including a hydrophobic group and including no hydrophilic groups (hydrophobic side-chain), and (meth)acrylic polymers having side chains including both a hydrophilic group and a hydrophobic group (amphiphilic side chains). Examples of hydrophilic groups include carboxyl group (—COOH) and sulfonic acid group (—SO$_3$H).

A (meth)acrylic polymer having a hydrophilic side chain and a hydrophobic side-chain has a monomer unit including a hydrophilic group and including no hydrophobic groups, and a monomer unit including a hydrophobic group and including no hydrophilic groups. Throughout the present specification, a (meth)acrylic monomer is one comprising an ethylenic unsaturated group (CR=CH$_2$—, where R is a hydrogen atom or a methyl group) as a reactive site in a (meth)acrylic group, and a side chain group bonded to the ethylenic unsaturated group.

The hydrophobic group may be bonded to the main chain through an ester bond (—COO—). Alkyl groups may be mentioned as hydrophobic groups. The number of carbon atoms in an alkyl group as a hydrophobic group may be 1 to 22, for example.

A (meth)acrylic polymer having a hydrophilic side chain and a hydrophobic side-chain may have (meth)acrylic acid and an alkyl (meth)acrylate ester as monomer units. Particularly preferred examples for (meth)acrylic polymers having a hydrophilic side chain and a hydrophobic side-chain include (Acrylates/Beheneth-25 Methacrylate) copolymers (for example, trade name: Aculyn 28), among which some are preferably used in combination with the base sodium hydroxide for neutralization.

A (meth)acrylic polymer having amphiphilic side chains has a monomer unit including both a hydrophilic group and a hydrophobic group. Amphiphilic side chains may be bonded to the main chain through amide bonds (—CONH—). An amphiphilic side chain may have a sulfonic acid group as the hydrophilic group and an alkylene group as the hydrophobic group. The number of carbon atoms of the alkylene group in the amphiphilic side chain may be 3 to 6, for example, and the alkylene group may be —$C(CH_3)_2$—$CH_2$—, for example. The amphiphilic side chains may also have an alkylsulfonic acid group (for example, —$C(CH_3)_2$—$CH_2$—$SO_3H$).

A (meth)acrylic polymer having amphiphilic side chains may be a (meth)acrylic polymer having a monomer unit that is a (meth)acrylamide substituted with substituents including a hydrophilic group and a hydrophobic group. The aforementioned substituents include alkyl-substituted aminoalkylsulfonic acid groups such as alkyl-substituted taurine groups. Examples of alkyl-substituted taurine groups include dimethyltaurine group (—NH—$C(CH_3)_2$—$CH_2$—$SO_3H$). The alkyl-substituted taurine group forms a side chain and has —$SO_3H$ (or its salt) as a hydrophilic group and the portion between —NH and —$SO_3H$ (or its salt) as the hydrophobic group.

The (meth)acrylic polymer having amphiphilic side chains may also have a monomer unit (another monomer unit) other than the amphiphilic monomer unit. Examples of other monomer units include monomer units derived from vinyl monomers, and monomer units derived from (meth) acrylic monomers. N-vinylpyrrolidone is an example of a vinyl monomer. Hydroxyethyl (meth)acrylate is an example of a (meth)acrylic monomer.

Examples of useful (meth)acrylic polymers having amphiphilic side chains include (meth)acrylic polymers having monomer units that are N-vinylpyrrolidone and a (meth) acrylamide substituted with a substituent including a hydrophilic group and a hydrophobic group. One such component is (acryloyldimethyltaurine ammonium/VP) copolymer (trade name: ARISTOFLEX AVC).

Examples of useful (meth)acrylic polymers having amphiphilic side chains include (meth)acrylic polymers having monomer units that are hydroxyethyl (meth)acrylate and a (meth)acrylamide substituted with a substituent including a hydrophilic group and a hydrophobic group. One such component is hydroxyethyl acrylate/acryloyldimethyltaurine Na) copolymer (trade name: SIMULGEL NS).

Useful hydrophobic group-modified hydrophilic polysaccharides include hydroxyalkylalkyl celluloses such as hydroxypropyl methyl cellulose, modified with the aforementioned hydrophobic groups. One such component is hydrophobized hydroxypropyl methyl cellulose, wherein the hydrophobic group is a stearoyl group (trade name: SANGELOSE 90L).

in a particular embodiment, the oil-in-water emulsion gel composition comprises a single type of amphiphilic polymer, or a combination of two or more types.

From the viewpoint of even more excellence in terms of the color vividness of the applied film and the nourishing effect, the oil-in-water emulsion gel composition comprises a hydrophobic group-modified hydrophilic urethane polymer, and a (meth)acrylic polymer having side chains including a hydrophilic group and a hydrophobic group as an amphiphilic polymer, or comprises a hydrophobic group-modified hydrophilic urethane polymer and a (meth)acrylic polymer having monomer units that are hydroxyethyl (meth) acrylate and a (meth)acrylamide substituted with a substituent including a hydrophilic group and a hydrophobic group.

The total content of the amphiphilic polymer(s) may be 0.01 mass % or greater or 0.03 mass % or greater, and no greater than 5.0 mass %, no greater than 2 mass %, no greater than 1.0 mass % or no greater than 0.5 mass %, based on the total mass of the oil-in-water emulsion gel composition. In a particular embodiment, the amphiphilic polymer(s) total content ranges from 0.01 mass % to 5.0 mass %, or from 0.03 mass % to 1.5 mass %, based on the total mass of the oil-in-water emulsion gel composition.
Coloring Materials The oil-in-water emulsion gel composition further comprises at least a coloring material. The term 'coloring material' according to the invention means a compound capable of producing a colored optical effect when it is formulated in sufficient quantity in a suitable cosmetic medium. The coloring material can be natural or non-natural, and can be soluble or non-soluble in water, soluble or non-soluble in oils agents, organic or inorganic.
In a particular embodiment, the coloring materials according to the invention are selected form the group consisting of dyes, pigments, nacres or pearlescent pigments, and mixtures thereof. In particular, the oil-in-water emulsion gel composition of the invention comprises coloring materials selected from the group consisting of dyes, pigments or mixtures thereof.
In a particular and preferred embodiment, the oil-in-water emulsion gel composition of the invention comprises at least a dye.
By "dyes" is meant in particular dyes conventionally used in the cosmetics field, distinct from food dyes used in food products.
Examples of dyes include Japan Red #227 (FDA: D&C RED33, CI:17200), and Japan Red #104 (FDA: D&C RED28, CI:45410), Japan Yellow #4 (FDA:D&C YELLOW 5, CI:19140), Japan Yellow #5 (FDA:D&C YELLOW 6, CI:15985) and Japan Blue #1 (FDA:D&C BLUE 1, CI:42090). Mention may be made also of Green 5, Green 3, Green 6, Orange 4, Red 4, Red 21, Red 22, Red 27, Red 28, Red 33, Red 40 and liposoluble dyes such as red Soudan, beta-carotene, brown Soudan, quinolin yellow and rococo. The dye(s) total content may be appropriately set according to the purpose of use of the oil-in-water emulsion gel composition. In a particular embodiment, the dye(s) total content ranges from 0.001 mass % to 1.0 mass % or from 0.01 mass % to 0.5 mass %, based on the total mass of the oil-in-water emulsion gel composition.

The oil-in-water emulsion gel composition may further comprise at least a pigment. By "pigment" is meant white or colored particles, mineral or organic, intended to color and/or opacify the applied film. A pigment may be an organic pigment or an inorganic pigment. Examples of pigments include organic pigments such as Japan Red #201 (FDA: D&C RED6, CI:15850), Japan Red #202 (FDA: D&C RED7, CI:15850) and Japan Red #226 (FDA: D&C RED30, CI:73360), D & C Red no 27; D & C Red no 22; D & C Red no 21; D & C Red no 28; D & C orange no 4; D & C Red no 33; D & C Yellow no 5; D & C Red no 36; D & C Yellow no 6; D &C Blue 1 and lakes with carmine of cochineal; and inorganic pigments such as titanium dioxide, black iron oxide, yellow iron oxide and red iron oxides and manganese violet. The pigment content may be appropriately set according to the purpose of use of the oil-in-water emulsion gel composition. In particular, the pigment(s) total content ranges from 0.01 mass % to 5.0 mass %, 0.01 mass % to 3.0 mass % or 0.01 mass % to 1.0 mass %, based on the total mass of the oil-in-water emulsion gel composition. The "nacres or pearlescent pigments" may be chosen from white nacreous pigments such as mica coated with titanium oxide, bismuth oxychloride; and colored nacreous pigments, such as titanium mica with iron oxides, titanium mica with an organic pigment of the aforementioned type, as well as pigments based on bismuth oxychloride. The pearlescent pigments may also have a base of silica, alumina, hydroxide alumina, synthetic mica, tin oxide, or borosilicate.

In a particular and preferred embodiment, the oil-in-water emulsion gel composition also contains a higher aliphatic monohydric alcohol, from the viewpoint of even more excellent color vividness of the applied film. A higher aliphatic monohydric alcohol is a chain alcohol of 6 or more carbon atoms having one hydroxyl group. A higher aliphatic monohydric alcohol may be any saturated alcohol lacking unsaturated bonds. The number of carbon atoms in a higher aliphatic monohydric alcohol may be 8 or more, 12 or more or 14 or more, and no more than 30, no more than 20 or no more than 18. Higher alcohols include cetyl alcohol, stearyl alcohol, behenyl alcohol, myristyl alcohol and lauryl alcohol. In a particular and preferred embodiment, the composition comprises cetyl alcohol, from the viewpoint of obtaining even more excellent color vividness of the applied film.

The higher aliphatic monohydric alcohol(s) total content may be 0.01 mass % or 0.1 mass % or greater, and no greater than 3 mass % or no greater than 1 mass %, based on the total mass of the oil-in-water emulsion gel composition. In particular, the higher aliphatic monohydric alcohol(s) total content ranges from 0.01 mass % to 3 mass % or 0.1 mass % to 1 mass %, based on the total mass of the oil-in-water emulsion gel composition.

Additional Components

The oil-in-water emulsion gel composition may also contain components other than the components mentioned above. Such other components may be antiseptic agents, pH regulators, aromatics, antioxidants, chelating agents and the like.

Phenoxyethanol is an example of an antiseptic agent. The antiseptic agent content may be appropriately set according to the purpose of use of the cosmetic, and the type of antiseptic agent. For example, the antiseptic agent content may be 0.01 mass % to 2.0 mass % or 0.1 mass % to 1.0 mass %, based on the total mass of the oil-in-water emulsion gel composition.

Viscosity

The viscosity of the oil-in-water emulsion gel composition may ranges from 20,000 to 400,000 cps at 25° C., preferably from 50,000 to 400,000 cps at 25° C. The viscosity of the oil-in-water emulsion gel cosmetic composition of the invention may be measured based on the shear viscosity using a rotating viscometer (Rheolab QC by Anton Paar GmbH), under conditions of 10 rpm, recording the viscosity measured at 25° C. for 7 minutes using an ST22-2V-19/110 measuring instrument.

If the viscosity of the oil-in-water emulsion gel composition at 25° C. is within this range, the color vividness, nourishing effect and stability of the applied film will be even more excellent. The viscosity of the oil-in-water emulsion gel composition at 25° C. may be, for example, 20,000 cps or higher, 30,000 cps or higher, 40,000 cps or higher, 50,000 cps or higher, 75,000 cps or higher, 100,000 cps or higher, 120,000 cps or higher, 140,000 cps or higher or 150,000 cps or higher, and no higher than 400,000 cps, no higher than 350,000 cps, no higher than 300,000 cps, no higher than 250,000 cps, no higher than 200,000 cps or no higher than 180,000 cps. In a particular embodiment, the viscosity of the oil-in-water emulsion gel composition ranges from 20,000 to 400,000 cps at 25° C., in particular from 30,000 to 350,000 cps, preferably from 40,000 to 300,000 cps and more preferably from 50,000 to 250,000 cps at 25° C. In a preferred embodiment, the viscosity of the oil-in-water emulsion gel composition at 25° C. ranges from 75,000 to 300,000 cps, 100,000 to 300,000 cps or 140,000 cps to 300,000 cps, from the viewpoint of even more excellence in terms of the color vividness of the applied film, the nourishing effect, and stability.

Emulsification Process

In a particular embodiment, the oil-in-water emulsion gel composition is obtainable by emulsification at a pressure of 50 MPa or higher. The pressure during emulsification may be, for example, 100 MPa or greater or 150 MPa or greater, and no greater than 500 MPa, no greater than 400 MPa, no greater than 300 MPa or no greater than 250 MPa, and it may be 200 MPa. The temperature during emulsification may be 20° C. or higher or 30° C. or higher, and no higher than 80° C., no higher than 70° C. or no higher than 40° C., for example.

In a particular and preferred embodiment, the emulsification is carried out with a high pressure homogenizer. A high pressure homogenizer is an apparatus that carries out emulsification by pressurizing a fluid with a pump and ejecting it through fine slits provided in a flow channel. As high pressure homogenizer, mentioned may be made of the Star Burst Mini: by Sugino Machine, Ltd.

The method for producing the oil-in-water emulsion gel composition of this embodiment includes a step of high-pressure emulsification of a liquid mixture containing at least an oil agent, water and an anionic surfactant, for example. Each of the components may be added to the mixture before high-pressure emulsification, or they may be added to the emulsified liquid obtained after high-pressure emulsification.

The method for the oil-in-water emulsion gel composition of this embodiment may comprise a step of mixing a first solution including the water and anionic surfactant and a second solution including the oil agent, to obtain a liquid mixture including the oil agent, water and anionic surfactant (mixing step), and a step of high-pressure emulsification of the liquid mixture to obtain an emulsified liquid (high-pressure emulsification step). Each of the components may be added by admixture with the first solution, or they may be added by admixture with the second solution, or they may be added by admixture with the liquid mixture, or they may be added by admixture with the emulsified liquid.

From the viewpoint of obtaining even more excellence in terms of the color vividness of the applied film and the nourishing effect, the amphiphilic polymer may be added by admixture at least with the first solution, or it may be added by admixture with the emulsified liquid in addition to the first solution.

The polyol is preferably added to the oil-in-water emulsion gel composition by admixture with the first solution. The coloring material such as dyes and pigments are preferably added to the oil-in-water emulsion gel composition by admixture with the emulsified liquid. The higher aliphatic monohydric alcohol is preferably added to the oil-in-water emulsion gel composition by admixture with the second solution.

The amphiphilic polymer (first amphiphilic polymer) to be mixed with the first solution may be of the same type as or a different type than the amphiphilic polymer (second amphiphilic polymer) to be mixed with the emulsified liquid, but it is preferably of a different type. The first amphiphilic polymer preferably includes a hydrophobic group-modified hydrophilic urethane polymer and/or a (meth)acrylic polymer having a side chain that includes a hydrophilic group and a hydrophobic group, and the second amphiphilic polymer preferably includes a (meth)acrylic polymer with a side chain including a hydrophobic group.

EXAMPLES

The invention will now be illustrated by examples, with the understanding that the invention is not meant to be limited to these examples.

<Preparation of Oil-In-Water Cosmetics for the Examples>
The component listed in column A of the tables (component A) and the component listed in column B of the tables (component B) were mixed and stirred at 70° C. using a homogenizer. The component listed in column C of the tables (component C) was then mixed at 70° C. with a homogenizer, and was combined with the mixture of component A and component B and mixed at 70° C. with a homogenizer. The mixture of components A to C was cooled to 30° C. and then subjected to high-pressure emulsification using a high pressure homogenizer (for example, a Star Burst Mini: by Sugino Machine, Ltd.). The pressure during emulsification was 200 MPa for Examples 1, 4 to 17 and 19 to 20, 50 MPa for Example 2, and 100 MPa for Example 3. For Example 9, Example 14 and Example 20, the component listed in column D of the tables (component D) was further added to the mixture at room temperature, after the high-pressure emulsification. The component listed in column E of the tables (component E) was added to the mixture after high-pressure emulsification, or after addition of component D, and mixed with a homogenizer. The oil-in-water cosmetics for Examples 1 to 17 and 19 to 20 were thus obtained.

An oil-in-water cosmetic for Example 18 was obtained in the same manner as Example 1, except that the component listed in column B of the tables (component B) was not added, and the component listed in column F of the tables (component F) was added, together with component E, to the mixture after high-pressure emulsification.

The oil-in-water cosmetics of Examples 1 to 20 obtained by the production method described above were all emulsion gel compositions. Their gel form was confirmed by a test of placing 0.5 g of the oil-in-water emulsion composition on an inclined surface inclined at 30° C. with respect to the horizontal, and confirming lack of flow for 1 hour under conditions of 25° C. Confirmation of lack of flow of the oil-in-water emulsion gel composition was made visually.

The contents (mass %) of each component listed in Tables 1 to 3 are the contents with respect to the total mass of the oil-in-water emulsion gel composition.

<Preparation of Oil-In-Water Cosmetics for the Comparative Examples>

An oil-in-water cosmetic for Comparative Example 1 was obtained in the same manner as Example 18, except that it does not contain the (PEG-240/decyl tetradeceth-20/HDI) copolymer corresponding to the amphiphilic polymer, which is an essential feature of the compositions of the invention.

An oil-in-water cosmetic for Comparative Example 2 was obtained in the same manner as Example 1, except that it contains a nonionic surfactant (PEG-60 hydrogenated castor oil) instead of an anionic surfactant (sodium stearoylglutamate) which is an essential feature of the compositions of the invention.

None of the oil-in-water cosmetics of Comparative Examples 1 and 2 obtained by the production method described above were gel compositions. This was confirmed by the same method used for the oil-in-water emulsion gel composition of the Examples.

<Viscosity Measurement>
The viscosity of the oil-in-water emulsion gel composition of the Examples and Comparative Examples were measured based on the shear viscosity using a rotating viscometer (Rheolab QC by Anton Paar GmbH), under conditions of 10 rpm, recording the viscosity measured at 25° C. for 7 minutes using an ST22-2V-19/110 measuring instrument.

<Organoleptic Evaluation>
An organoleptic evaluation was conducted for the oil-in-water cosmetics of the Examples and Comparative Examples. The evaluation parameters were: watery fresh sensation, color vividness of applied film (makeup film), and nourishing effect, and the cosmetics were used once on the lips by an evaluation panel of 10 cosmetic experts from an organization to which the present inventors belong (ages 25 to 55), with the following scale being used for evaluation. The results are shown in Tables 1 to 3. Overall excellence was considered to be an evaluation of A to C.

A: Excellent
B: Better
C: Good
D: Not passable
E: Not good
F: Bad

The organoleptic evaluation was conducted by applying the oil-in-water cosmetic to the lips using a "Flocky-Tip" bearing the adhered oil-in-water cosmetic. A Flocky-Tip is an application tool commonly used for application of liquid lipsticks. The Flocky-Tip was impregnated with a suitable amount of the oil-in-water cosmetic of the Example or Comparative Example, adhering the oil-in-water cosmetic to the Flocky-Tip.

A better evaluation for watery fresh sensation indicates greater freshness and less burdensome sensation. The color vividness of the applied film (makeup film) was evaluated on the index of color vividness deriving from uniformity of the applied film (cosmetic film). A better evaluation for color vividness of the applied film (makeup film) indicates easier formation of a uniform cosmetic film, and therefore a greater sense of color. The nourishing effect was evaluated on the indices of moisturized feel and non-dry feel after the cosmetic dried. A better evaluation for the nourishing effect indicates less of a dry feel and a more moisturized sensation after the oil-in-water cosmetic has dried.

The stability of the oil-in-water emulsified cosmetics of the Examples and Comparative Examples was evaluated. The stability was evaluated by allowing the oil-in-water emulsified cosmetic to stand at 50° C. for 28 days, and visually observing the outer appearance of the oil-in-water emulsified cosmetic after standing. Upon observing the outer appearance, an evaluation of "B" was assigned when separation occurred in the oil-in-water emulsified cosmetic, and an evaluation of "A" was assigned when no change in outer appearance was apparent. Excellence of stability was considered to be an evaluation of A.

The table 1 illustrates 14 examples of oil-in water emulsion gel compositions of the invention. All these compositions comprise an oil agent, an anionic surfactant, polyols, an amphiphilic polymer, water, dyes and pigments, and optionally a second amphiphilic polymers (examples 9 and 14) or an higher aliphatic monohydric alcohol (cetyl alcohol in example 10). These compositions have good water fresh sensation, color vividness of applied film, nourishing effect, and good stability. The best performances are obtained with the compositions having two amphiphilic polymer of different type.

TABLE 1

| | | | Example | | | | | | | |
|---|---|---|---|---|---|---|---|---|---|---|
| | | | 1 | 2 | 3 | 4 | 5 | 6 | 7 | 8 |
| Composition | A | Sodium stearoylglutamate*[1] | 1.50 | 1.50 | 1.50 | 1.50 | 1.50 | 1.50 | 1.50 | 1.50 |
| | | Sodium lysine dilauroylglutamate*[2] | — | — | — | — | — | — | — | — |
| | | Pentylene glycol | 3.00 | 3.00 | 3.00 | 3.00 | 3.00 | 3.00 | 3.00 | 3.00 |
| | | Glycerin | 5.00 | 5.00 | 5.00 | 5.00 | 5.00 | 5.00 | 5.00 | 5.00 |
| | | Butylene glycol | 3.00 | 3.00 | 3.00 | 3.00 | 3.00 | 3.00 | 3.00 | 3.00 |
| | | Phenoxyethanol | 0.50 | 0.50 | 0.50 | 0.50 | 0.50 | 0.50 | 0.50 | 0.50 |
| | | Water | 17.00 | 17.00 | 17.00 | 17.00 | 17.00 | 17.00 | 27.00 | 12.00 |
| | B | Water | 7.90 | 7.90 | 7.90 | 7.90 | 7.90 | 7.90 | 7.90 | 7.90 |
| | | Butylene glycol | 2.00 | 2.00 | 2.00 | 2.00 | 2.00 | 2.00 | 2.00 | 2.00 |
| | | (PEG-240/decyl tetradeceth-20/HDI) copolymer*[3] | 0.10 | 0.10 | 0.10 | 0.10 | 0.10 | 0.10 | 0.10 | 0.10 |
| | C | Isododecane | 10.00 | 10.00 | 10.00 | — | — | — | 7.50 | 11.25 |
| | | Dimethicone | 5.00 | 5.00 | 5.00 | 40.00 | — | — | 3.75 | 5.63 |
| | | Methyltrimethicone*[7] | 10.00 | 10.00 | 10.00 | — | — | — | 7.50 | 11.25 |
| | | Squalane | 7.50 | 7.50 | 7.50 | — | 40.00 | — | 5.625 | 8.44 |
| | | Polyglyceryl-2 triisostearate | 7.50 | 7.50 | 7.50 | — | — | 40.00 | 5.625 | 8.44 |
| | | Cetyl alcohol | — | — | — | — | — | — | — | — |
| Composition | D | (Hydroxyethyl acrylate/acryloyl-dimethyltaurine Na) co-polymer, water, squalane, polysorbate 60, sorbitan isostearate*[8] | — | — | — | — | — | — | — | — |
| | E | Water | 17.54 | 17.54 | 17.54 | 17.54 | 17.54 | 17.54 | 17.54 | 17.54 |
| | | D&C RED 33 | 0.01 | 0.01 | 0.01 | 0.01 | 0.01 | 0.01 | 0.01 | 0.01 |
| | | D&C RED 28 | 0.10 | 0.10 | 0.10 | 0.10 | 0.10 | 0.10 | 0.10 | 0.10 |
| | | Water | 2.00 | 2.00 | 2.00 | 2.00 | 2.00 | 2.00 | 2.00 | 2.00 |
| | | Titanium dioxide, silica, alumina*[9] | 0.35 | 0.35 | 0.35 | 0.35 | 0.35 | 0.35 | 0.35 | 0.35 |
| | | Total content (mass %) | 100.00 | 100.00 | 100.00 | 100.00 | 100.00 | 100.00 | 100.00 | 100.00 |
| | | Viscosity (cps) | 118,400 | 68,230 | 105,100 | 25,920 | 71,280 | 77,450 | 19,110 | 79,810 |
| | | Oil agent content (mass %) | 40% | 40% | 40% | 40% | 40% | 40% | 30% | 45% |
| Evaluation | | Watery fresh sensation | A | A | A | A | A | A | A | B |
| | | Color vividness of applied film | B | C | B | C | C | C | C | C |
| | | Nourishing effect | B | B | B | C | B | B | C | A |
| | | Stability | A | A | A | A | A | A | A | A |

| | | | Example | | | | | |
|---|---|---|---|---|---|---|---|---|
| | | | 9 | 10 | 11 | 12 | 13 | 14 |
| Composition | A | Sodium stearoylglutamate*[1] | 1.50 | 1.50 | 3.00 | 1.00 | — | — |
| | | Sodium lysine dilauroylglutamate*[2] | — | — | — | — | 1.50 | 1.50 |
| | | Pentylene glycol | 3.00 | 3.00 | 3.00 | 3.00 | 3.00 | 3.00 |
| | | Glycerin | 5.00 | 5.00 | 5.00 | 5.00 | 5.00 | 5.00 |
| | | Butylene glycol | 3.00 | 3.00 | 3.00 | 3.00 | 3.00 | 3.00 |
| | | Phenoxyethanol | 0.50 | 0.50 | 0.50 | 0.50 | 0.50 | 0.50 |
| | | Water | 17.00 | 17.00 | 15.50 | 17.50 | 17.00 | 16.00 |
| | B | Water | 7.90 | 7.90 | 7.90 | 7.90 | 7.90 | 7.90 |
| | | Butylene glycol | 2.00 | 2.00 | 2.00 | 2.00 | 2.00 | 2.00 |
| | | (PEG-240/decyl tetradeceth-20/HDI) copolymer*[3] | 0.10 | 0.10 | 0.10 | 0.10 | 0.10 | 0.10 |

TABLE 1-continued

|  |  |  |  |  |  |  |  |  |
|---|---|---|---|---|---|---|---|---|
|  | C | Isododecane | 10.00 | 10.00 | 10.00 | 10.00 | 10.00 | 10.00 |
|  |  | Dimethicone | 5.00 | 5.00 | 5.00 | 5.00 | 5.00 | 5.00 |
|  |  | Methyltrimethicone*7 | 10.00 | 10.00 | 10.00 | 10.00 | 10.00 | 10.00 |
|  |  | Squalane | 7.50 | 7.50 | 7.50 | 7.50 | 7.50 | 7.50 |
|  |  | Polyglyceryl-2 triisostearate | 7.50 | 7.00 | 7.50 | 7.50 | 7.50 | 7.50 |
|  |  | Cetyl alcohol | — | 0.50 | — | — | — | — |
| Composition | D | (Hydroxyethyl acrylate/acryloyl-dimethyltaurine Na) co-polymer, water, squalane, polysorbate 60, sorbitan isostearate*8 | 0.25 | — | — | — | — | 1.00 |
|  | E | Water | 17.29 | 17.54 | 17.54 | 17.54 | 17.54 | 17.54 |
|  |  | D&C RED 33 | 0.01 | 0.01 | 0.01 | 0.01 | 0.01 | 0.01 |
|  |  | D&C RED 28 | 0.10 | 0.10 | 0.10 | 0.10 | 0.10 | 0.10 |
|  |  | Water | 2.00 | 2.00 | 2.00 | 2.00 | 2.00 | 2.00 |
|  |  | Titanium dioxide, silica, alumina*9 | 0.35 | 0.35 | 0.35 | 0.35 | 0.35 | 0.35 |
|  |  | Total content (mass %) | 100.00 | 100.00 | 100.00 | 100.00 | 100.00 | 100.00 |
|  |  | Viscosity (cps) | 155,700 | 109,300 | 242,000 | 71,220 | 29,800 | 131,200 |
|  |  | Oil agent content (mass %) | 40% | 40% | 40% | 40% | 40% | 40% |
| Evaluation |  | Watery fresh sensation | A | A | A | A | A | A |
|  |  | Color vividness of applied film | A | A | B | B | C | A |
|  |  | Nourishing effect | A | B | B | B | B | A |
|  |  | Stability | A | A | A | A | A | A |

The table 2 discloses 3 more examples of oil-in water emulsion gel compositions of the invention, wherein different amphiphilic polymers are illustrated. These 3 compositions have good water fresh sensation, color vividness of applied film, nourishing effect, and good stability.

TABLE 2

|  |  |  | Example | | |
|---|---|---|---|---|---|
|  |  |  | 15 | 16 | 17 |
| Composition | A | Sodium stearoylglutamate*1 | 1.50 | 1.50 | 1.50 |
|  |  | Pentylene glycol | 3.00 | 3.00 | 3.00 |
|  |  | Glycerin | 5.00 | 5.00 | 5.00 |
|  |  | Butylene glycol | 3.00 | 3.00 | 3.00 |
|  |  | Phenoxyethanol | 0.50 | 0.50 | 0.50 |
|  |  | Water | 17.00 | 17.00 | 16.58 |
|  | B | Water | 7.70 | 7.70 | 7.90 |
|  |  | Butylene glycol | 2.00 | 2.00 | 2.00 |
|  |  | (PEG-150/decyl alcohol/SMDI) copolymer, propylene glycol, water*4 | 0.30 | — | — |
|  |  | (PEG-150/stearyl alcohol/SMDI) copolymer, water, methylcyclodextrin, methyl isothiazolinone, caprylyl glycol*5 | — | 0.30 | — |
|  |  | (Acrylates/Beheneth-25 methacrylate) copolymer, water*6 | — | — | 0.50 |
|  |  | Sodium hydroxide | — | — | 0.02 |
|  | C | Isododecane | 10.00 | 10.00 | 10.00 |
|  |  | Dimethicone | 5.00 | 5.00 | 5.00 |
|  |  | Methyltrimethicone*7 | 10.00 | 10.00 | 10.00 |
|  |  | Squalane | 7.50 | 7.50 | 7.50 |
|  |  | Polyglyceryl-2 triisostearate | 7.50 | 7.50 | 7.50 |
|  | E | Water | 17.54 | 17.54 | 17.54 |
|  |  | D&C RED 33 | 0.01 | 0.01 | 0.01 |
|  |  | D&C RED 28 | 0.10 | 0.10 | 0.10 |
|  |  | Water | 2.00 | 2.00 | 2.00 |
|  |  | Titanium dioxide, silica, alumina*9 | 0.35 | 0.35 | 0.35 |
|  |  | Total content (mass %) | 100.00 | 100.00 | 100.00 |
|  |  | Viscosity (cps) | 76,490 | 45,640 | 88,130 |
|  |  | Oil agent content (mass %) | 40% | 40% | 40% |

TABLE 2-continued

|  |  | Example | | |
|---|---|---|---|---|
|  |  | 15 | 16 | 17 |
| Evaluation | Watery fresh sensation | A | A | A |
|  | Color vividness of applied film | B | C | B |
|  | Nourishing effect | B | B | B |
|  | Stability | A | A | A |

The table 3 discloses 3 more examples of oil-in water emulsion gel compositions of the invention and 2 additional comparative examples, wherein comparative example 1 illustrates the case wherein the composition does not contain any amphiphilic polymer and the comparative example 2 illustrates the case wherein the surfactant is not an anionic surfactant.

The results of the comparative examples demonstrate that the presence of an anionic surfactant and the presence of an amphiphilic polymer are both necessary, ie essential features, in an oil-in-water emulsion comprising oil agent, polyols, dyes and pigments, to obtain an oil-in-water emulsion gel composition according to the invention, having

TABLE 3

|  |  |  | Example | | | Comp. Example | |
|---|---|---|---|---|---|---|---|
|  |  |  | 18 | 19 | 20 | 1 | 2 |
| Composition | A | Sodium stearoylglutamate*[1] | 1.50 | 1.50 | 1.50 | 1.50 | — |
|  |  | PEG-60 hydrogenated castor oil | — | — | — | — | 1.50 |
|  |  | Pentylene glycol | 3.00 | 3.00 | 3.00 | 3.00 | 3.00 |
|  |  | Glycerin | 5.00 | 5.00 | 5.00 | 5.00 | 5.00 |
|  |  | Butylene glycol | 3.00 | 3.00 | 3.00 | 3.00 | 3.00 |
|  |  | Phenoxyethanol | 0.50 | 0.50 | 0.50 | 0.50 | 0.50 |
|  |  | Water | 17.00 | 17.00 | 17.00 | 17.00 | 17.00 |
|  | B | Water | — | 7.90 | 7.90 | — | 7.90 |
|  |  | Butylene glycol | — | 2.00 | 2.00 | — | 2.00 |
|  |  | (PEG-240/decyl tetradeceth-20/HDI) copolymer*[3] | — | — | — | — | 0.10 |
|  |  | (Acryloyldimethyltaurineammonium/VP) copolymer*[10] | — | 0.10 | — | — | — |
|  |  | Hydroxypropyl Methylcellulose Stearoxy Ether*[11] | — | — | 0.10 | — | — |
|  | C | Isododecane | 10.00 | 10.00 | 10.00 | 10.00 | 10.00 |
|  |  | Dimethicone | 5.00 | 5.00 | 5.00 | 5.00 | 5.00 |
|  |  | Methyltrimethicone*[7] | 10.00 | 10.00 | 10.00 | 10.00 | 10.00 |
|  |  | Squalane | 7.50 | 7.50 | 7.50 | 7.50 | 7.50 |
|  |  | Polyglyceryl-2 triisostearate | 7.50 | 7.50 | 7.50 | 7.50 | 7.50 |
|  | D | (Hydroxyethyl acrylate/acryloyldimethyltaurine Na) co-polymer, water, squalane, polysorbate 60, sorbitan isostearate*[8] | — | — | 1.5 | — | — |
|  |  | Water | 17.54 | 17.54 | 16.04 | 17.54 | 17.54 |
|  |  | D&C RED 33 | 0.01 | 0.01 | 0.01 | 0.01 | 0.01 |
|  | E | D&C RED 28 | 0.10 | 0.10 | 0.10 | 0.10 | 0.10 |
|  |  | Water | 2.00 | 2.00 | 2.00 | 2.00 | 2.00 |
| Composition |  | Titanium dioxide, silica, alumina*[9] | 0.35 | 0.35 | 0.35 | 0.35 | 0.35 |
|  |  | Water | 7.90 | — | — | 8.00 | — |
|  | F | Butylene glycol | 2.00 | — | — | 2.00 | — |
|  |  | (PEG-240/decyl tetradeceth-20/HDI) copolymer*[3] | 0.10 | — | — | — | — |
|  |  | Total content (mass %) | 100.00 | 100.00 | 100.00 | 100.00 | 100.00 |
|  |  | Viscosity (cps) | 54,020 | 49,840 | 325,800 | 2,408 | — |
|  |  | Oil agent content (mass %) | 40% | 40% | 40% | 40% | 40% |
| Evaluation |  | Watery fresh sensation | A | A | A | A | A |
|  |  | Color vividness of applied film | C | C | B | F | F |
|  |  | Nourishing effect | B | C | B | F | F |
|  |  | Stability | A | A | A | B | B |

*[1]AMISOFT HS-11PF (trade name of Ajinomoto Co., Inc.),
*[2]PELICER L-30 (trade name of Asahi Kasei Corp.),
*[3]Adeka Corp., NOL GT-700 (trade name of Adeka Corp.),
*[4]ACULYN 44 (trade name of Dow Chemical Corp.),
*[5]ACULYN 46N (trade name of Dow Chemical Corp.),
*[6]ACULYN 28 (trade name of Dow Chemical Corp.),
*[7]TMF-1.5 (trade name of Shin-Etsu Chemical Co., Ltd.),
*[8]SIMULGEL NS (trade name of Seppic Co., Ltd.),
*[9]SYMPHOLIGHT WW (trade name of JGC Corporation),
*[10]ARISTOFLEX AVC (trade name of CLARIANT),
*[11]SANGELOSE 90L (trade name of Daido Chemical Corporation).

good water fresh sensation, color vividness of applied film, nourishing effect, and good stability.

The invention claimed is:

1. An oil-in-water emulsion gel composition comprising an oil agent, water, a polyol, an anionic amino acid surfactant, a mixture of amphiphilic polymers and a coloring material, wherein the oil agent(s) total content with respect to the total mass of the oil-in-water emulsion gel composition is 25 mass % or greater, wherein the mixture of amphiphilic polymers comprises a hydrophobic group-modified hydrophilic urethane polymer and a (meth)acrylic polymer having monomer units that are hydroxyethyl (meth)acrylate and a (meth) acrylamide substituted with a substituent comprising a hydrophilic group and a hydrophobic group.

2. The oil-in-water emulsion gel composition according to claim 1, wherein the polyol is a $C_1$-$C_6$ polyol.

3. The oil-in-water emulsion gel cosmetic composition according to claim 1, wherein the polyol is selected from the group consisting of pentylene glycol, butylene glycol, glycerin, propanediol, dipropylene glycol, sorbitol, and mixtures thereof.

4. The oil-in-water emulsion gel composition according to claim 1, wherein the total content of the oil agent(s) ranges from 30 mass % to 50 mass % based on the total mass of the oil-in-water emulsion gel composition.

5. The oil-in-water emulsion gel cosmetic composition according to claim 1, wherein the hydrophobic group-modified hydrophilic urethane polymer comprises a hydrophobic group-modified polyether urethane comprising polyethylene glycol or polypropylene glycol as a glycol component.

6. The oil-in-water emulsion gel composition according to claim 1, wherein the coloring material is selected from the group consisting of dyes, pigments, nacres and pearlescent pigments, and mixtures thereof.

7. The oil-in-water emulsion gel composition according to claim 1, further comprising a chain alcohol of 6 or more carbon atoms having one hydroxyl group.

8. The oil-in-water emulsion gel composition according to claim 1, wherein the viscosity ranges from 20,000 to 400, 000 cps.

9. The oil-in-water emulsion gel composition according to claim 1, which is for lips.

10. The oil-in-water emulsion gel composition according to claim 1, wherein the composition is obtained by emulsification at a pressure of 50 MPa or greater.

11. A cosmetic process for caring for and/or making-up keratinic materials, comprising applying onto keratinic materials, the oil-in-water emulsion gel composition as defined in claim 1.

* * * * *